US00RE50361E

(19) United States
(12) Reissued Patent
O'Mahony

(10) Patent Number: US RE50,361 E
(45) Date of Reissued Patent: Apr. 8, 2025

(54) PERCUTANEOUS ELECTRICAL PHRENIC NERVE STIMULATION SYSTEM

(71) Applicant: Stimdia Medical, Inc., Bloomington, MN (US)

(72) Inventor: John O'Mahony, Plymouth, MN (US)

(73) Assignee: Stimdia Medical, Inc., Mendota Heights, MN (US)

(21) Appl. No.: 17/977,372

(22) Filed: Oct. 31, 2022

Related U.S. Patent Documents

Reissue of:
(64) Patent No.: 11,207,517
Issued: Dec. 28, 2021
Appl. No.: 16/028,988
Filed: Jul. 6, 2018

U.S. Applications:
(60) Provisional application No. 62/529,045, filed on Jul. 6, 2017.

(51) Int. Cl.

| | |
|---|---|
| ***A61N 1/00*** | (2006.01) |
| ***A61B 5/08*** | (2006.01) |
| ***A61B 5/085*** | (2006.01) |
| ***A61B 5/087*** | (2006.01) |
| ***A61M 16/00*** | (2006.01) |

(Continued)

(52) U.S. Cl.
CPC ..... *A61N 1/36031* (2017.08); *A61B 5/085* (2013.01); *A61B 5/087* (2013.01); *A61M 16/00* (2013.01); *A61N 1/3601* (2013.01); *A61B 5/0803* (2013.01); *A61M 2016/0021* (2013.01); *A61M 2016/0027* (2013.01); *A61M 2016/0036* (2013.01); *A61M 16/0833* (2014.02); *A61M 2205/054* (2013.01); *A61M 2205/18* (2013.01); *A61M 2205/505* (2013.01); *A61M 2230/42* (2013.01); *A61N 1/0551* (2013.01); *A61N 1/08* (2013.01); *A61N 1/3611* (2013.01)

(58) Field of Classification Search
CPC ..... A61N 1/36031; A61B 5/085; A61B 5/087
See application file for complete search history.

(56) References Cited

U.S. PATENT DOCUMENTS

| | | | |
|---|---|---|---|
| 3,773,051 | A | 11/1973 | Holcomb et al. |
| 6,484,057 | B2 | 11/2002 | Ideker et al. |

(Continued)

FOREIGN PATENT DOCUMENTS

| | | |
|---|---|---|
| JP | S61-502518 | 11/1986 |
| JP | 2015-519975 | 8/2015 |
| WO | 2014207623 | 12/2014 |

OTHER PUBLICATIONS

Banner, "Respiratory muscle loading and the work of breathing," Apr. 1995, Journal of Cardiothoracic and Vascular Anesthesia, 9(2):192-204 (First page only).

(Continued)

*Primary Examiner* — Robert L Nasser
(74) *Attorney, Agent, or Firm* — Fish & Richardson P.C.

(57) ABSTRACT

A percutaneous electrical phrenic nerve stimulation (PEPNS) system that measures the patient Work of Breathing (WOB) of each type of ventilator breath and determines when to deliver electrical stimulus based upon the measured WOB. The PEPNS system alters its behavior based upon the type and origin of the ventilator breath delivered and provides warnings for certain identified interactions between the ventilator and the patient.

38 Claims, 9 Drawing Sheets

(51) Int. Cl.

| | |
|---|---|
| ***A61M 16/08*** | (2006.01) |
| ***A61N 1/05*** | (2006.01) |
| ***A61N 1/08*** | (2006.01) |
| ***A61N 1/36*** | (2006.01) |

(56) References Cited

U.S. PATENT DOCUMENTS

| | | | | |
|---|---|---|---|---|
| 7,283,875 | B2 | 10/2007 | Larsson et al. | |
| 7,792,585 | B1 | 9/2010 | Shelchuk | |
| 8,406,885 | B2 | 3/2013 | Ignagni et al. | |
| 8,597,198 | B2 | 12/2013 | Sanborn | |
| 8,903,510 | B2 | 12/2014 | Rosenberg et al. | |
| 9,242,088 | B2 | 1/2016 | Thakkar et al. | |
| 9,333,363 | B2 | 5/2016 | Hoffer et al. | |
| 9,682,235 | B1 | 6/2017 | O'Mahony et al. | |
| 10,165,966 | B2 * | 1/2019 | Banner | A61B 5/087 |
| 2009/0024176 | A1 * | 1/2009 | Yun | A61N 1/3627 607/20 |
| 2012/0290036 | A1 | 11/2012 | Karamanoglu et al. | |
| 2013/0030496 | A1 | 1/2013 | Karamanoglu et al. | |
| 2014/0123979 | A1 * | 5/2014 | Doyle | A61M 16/04 128/204.23 |
| 2015/0045810 | A1 | 2/2015 | Hoffer et al. | |
| 2015/0045848 | A1 | 2/2015 | Cho et al. | |
| 2015/0265833 | A1 | 9/2015 | Meyyappan et al. | |
| 2015/0283340 | A1 | 10/2015 | Zhang et al. | |
| 2015/0367127 | A1 * | 12/2015 | Meyyappan | A61N 1/3601 128/204.23 |
| 2016/0067484 | A1 * | 3/2016 | Francois | A61H 9/0078 601/41 |
| 2016/0220822 | A1 | 8/2016 | Hoffer et al. | |
| 2016/0310730 | A1 * | 10/2016 | Martins | A61M 16/024 |
| 2017/0165480 | A1 | 6/2017 | O'Mahony | |

OTHER PUBLICATIONS

Brochard et al., "Clinical review: Respiratory monitoring in the ICU—a consensus of 16," Crit Care, Dec. 12, 2012, 16(2):219, 14 pages.

Extended European Search Report in European Appln No. 18828381, dated Mar. 2, 2021, 6 pages.

International Search Report and Written Opinion in International Appln. No. PCT/US2018/041056, mailed on Sep. 17, 2018, 6 pages.

Levy et al., "Work of breathing as a weaning parameter in mechanically ventilated patients," Chest, Oct. 1995, 108(4):1018-20 (abstract only).

Apr. 13, 2017 PCT Search Report (Serial No. PCT/US16/66542)—Our Matter 5518.

Apr. 13, 2018 USPTO Office Action (U.S. Appl. No. 15/601,335)—Our Matter 5565.

Jun. 27, 2018 USPTO Office Action (U.S. Appl. No. 15/601,315)—Our Matter 5564.

* cited by examiner

PERCUTANEOUS ELECTRICAL PHRENIC NERVE STIMULATION SYSTEM

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

The present application *is a reissue application of U.S. Pat. No. 11,207,517* (*Ser. No. 16/028,988*) *filed on Jul. 6, 2018, which* is a Utility filing claiming priority to U.S. Provisional Application No. 62/529,045, filed Jul. 6, 2017 and entitled: "PEPNS System with Assisted Breathing", the entire contents of which is incorporated herein by reference.

FIELD OF THE INVENTION

Embodiments of the present disclosure are directed to medical devices, systems and their methods of use for providing noninvasive percutaneous and subcutaneous electrical stimulation of the phrenic nerve to a patient subjected to mechanical ventilation, in order to mitigate the effects of ventilator-induced diaphragmatic dysfunction. Such embodiments are collectively referred to as percutaneous electrical phrenic nerve stimulation systems (PEPNS) systems. Embodiments include devices for controlling, activating, and otherwise interacting with the phrenic nerve, and thereby the diaphragm, of a patient while the patient is undergoing mechanical ventilation and determining when best to stimulate. Systems are disclosed for differentiating between the various types of ventilator delivered breaths and alters its behavior based upon the type and origin of the ventilator breath delivered and provides warnings for certain identified interactions between the ventilator and the patient.

BACKGROUND

Mechanical ventilation (MV) is used clinically to maintain gas exchange in patients that require assistance in maintaining adequate alveolar ventilation. Common indications for MV include respiratory failure, heart failure, surgery, etc. Although MV can be a life-saving intervention for patients suffering from respiratory failure, prolonged MV can promote diaphragmatic atrophy and contractile dysfunction, which is referred to as ventilator-induced diaphragm dysfunction (VIDD). Extended time on the ventilator may result in VIDD and thereby increase health care costs and greatly increase patient morbidity and mortality. Research reveals that 18-24 h on MV is sufficient to develop VIDD in both laboratory animals and humans.

Over two million patients are ventilated in United States each year representing 36% of the ICU population. The estimated annual cost to manage ventilated patients in the US each year is 27 billion representing 12% of all hospital costs. It has been found that approximately 60% of the ICU patient population intubated are scheduled for extubation and weaning. Unfortunately, nearly 45% of patients receiving invasive ventilation therapy in the ICU have difficulty weaning and develop some form of dependency on the ventilator. This often leads to the need to extend the patients ICU/CCU stay beyond what is typically required for the original medical condition since many encounter prolonged weaning periods. The projected number of patients requiring prolonged acute mechanical ventilation on an annual basis in the US is expected to grow to be greater than 600,000 patients by the year 2020 with the overall cost of managing these patients exceeding $64 billion.

Animal models have shown that maintaining some level of diaphragm activity using electrical stimulation to keep the diaphragm working when on a mechanical ventilator is enough to prevent or reduce atrophy. The current medical practice is to minimize sedation levels and place patients on mixed modes of ventilation such as SIMV (Synchronized Intermittent Mandatory Ventilation) as soon as possible. Unfortunately having a patient breath spontaneously or in assist mode from the initiation of ventilation is not always possible due to the level of sedation and/or disease state. In these patients VIDD is highly likely and weaning times are much longer.

When the patient is on a ventilator and they are unable to generate inspiratory effort, phrenic nerve pacing is a viable alternative to control the level of effort exerted by the patient and also in cases where the patient has become ventilator dependent and requires a training regime of pacing to strengthen their muscles. Pacing the phrenic nerve in patients who have suffered a paralyzing spine injury and have also lost the ability to breath has be shown to reverse the effect of diaphragm atrophy over months of training where the diaphragm may not have been used in years. From this data and the data on weaning of hospitalized patients, who have been on long term ventilation, we know that rehabilitation of the diaphragm muscle takes a much longer time to rehabilitate that it does to atrophy. Typically, 60% of the ICU length of stay for ventilated patients is devoted to weaning. Initiating electrical stimulation of the diaphragm early in the regime of ventilation will most likely have the most profound effect on reducing time to extubation.

Electrically stimulating a patient's diaphragm when the patient is already initiated an assist or spontaneous breath may not always be desirable. It is believed that in some cases the patient may be uncomfortable or become agitated by the intrusion of electrical stimulation. When patients begin to regain breathing control on a ventilator, it usually means that they are becoming more alert or they are reacting to the intrusion of ventilation. There is a need for the diaphragm pacing system when used in conjunction with ventilation to recognize that the patient is beginning to actively breath of their own volition and to allow the operator to have the diaphragm pacing system respond with the desired reaction.

SUMMARY

The PEPNS is not directly aware of the mode or modes of ventilation the mechanical ventilator has been programmed to deliver. This would require communication or implementing the desired functions of the PEPNS System with the ventilator which is not easily implemented given the range of ventilator models and brands currently available on the market. Each ventilator brand uses its own protocol for communicating settings with external devices and some older ventilators may not even have such a communication feature. Many modes of ventilation have a manufacturers specific implementation further complicating any potential communication. The PEPNS System is currently implemented as being separate from the ventilator but could obviously be implemented as part of the ventilator hardware eliminating many of the issues with determining the mode of ventilation and breath types being implemented in real time.

Implemented as a separate device is also a near impossible task to differentiate between many of the different types of the breath waveforms, manufacturer specific implementations by examining the waveform shapes in terms of flow and pressure because many of the breath types may result in similar waveforms in terms of flow and pressure. For instance, it's possible to make a descending flow ramp, volume-controlled breath looks the same as a pressure rise limited pressure control breath in terms of its pressure and flow traces.

There is a need for an external diaphragm pacing system used in conjunction with ventilation to determine when a patient is being delivered a mandatory breath, breathing in assist or spontaneous mode of ventilation. It is a goal to distinguish when the patient is exercising their own diaphragm independent of electrical stimulation, to what level of effort and to implement a course of action based upon the clinicians' mandate.

There are a number of potential ways or combination of ways that the clinician would prefer the PEPNS System to respond if the patient begins to control their own breath rate resulting in the ventilator delivering assist or spontaneous breaths. These preferential elements and/or functions are provided by the embodiments of the PEPNS system described herein and include:

1. Cease or desist electrical stimulation when the patient actively takes a breath. Do not perform any electrical stimulation on a patient-initiated breath.
2. Alert the operator when the patient is actively breathing. Generate an alarm bringing the operators attention to the fact that the patient is now initiating breaths.
3. Provide electrical stimulation on mandatory breaths only at the desired breath count rate count on mandatory breaths only.
4. Provide electrical stimulation if the work of breathing (WOB) measured for a particular breath or on a minute basis does not reach the desired level on a spontaneous or assist breaths on mandatory breaths only. Unfortunately, it's possible to set a pressure support level that will stop the patient from actively breathing on their own.
5. Alert the operator if the WOB level for assist and spontaneous breaths is not being achieved.
6. Continue stimulation independent of any breath type.

BRIEF DESCRIPTION OF THE DRAWINGS

Throughout the several views of the drawing identified below reference numerals indicate identical structures.

DETAILED DESCRIPTION

Figure 1A:
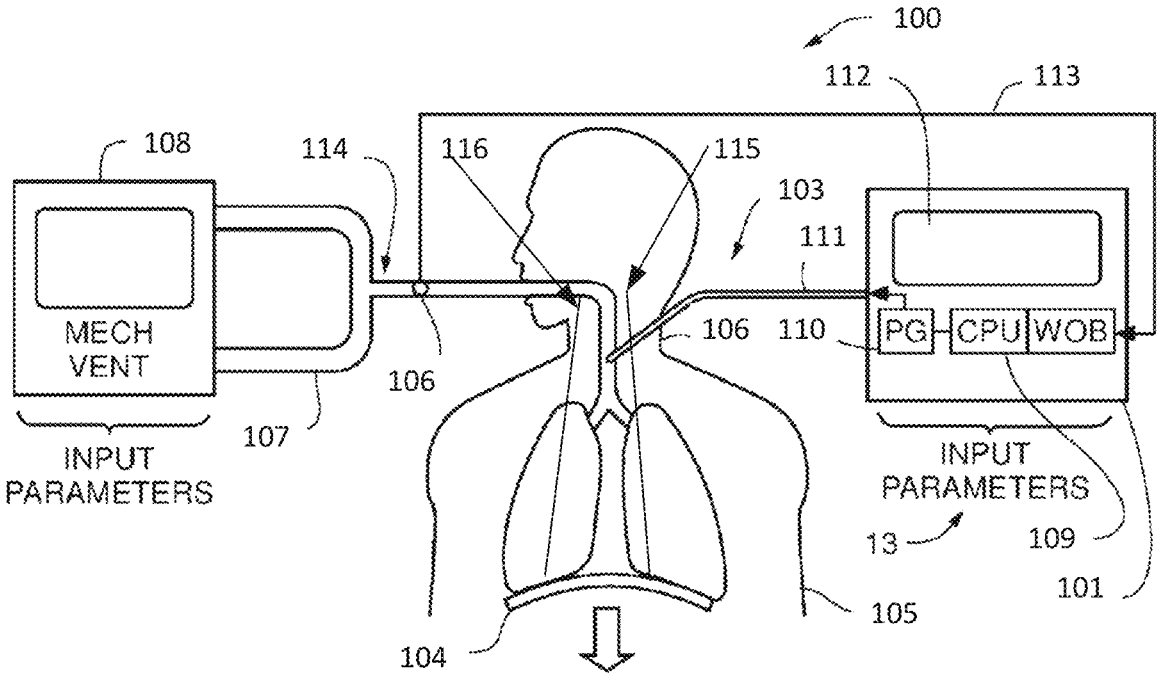
FIG. 1a is a schematic view of an embodiment of the PEPNS system shown in use with a patient and ventilator.

Before proceeding with the detailed description of the various embodiments of the PEPNs system and its features as shown in FIGS. 1-8, it is necessary to first provide some definitions of key terms that are used herein, so as to ensure a uniformity of meaning and avoid possible idiosyncratic use of the same or similar terms as they may be used in the context of ventilator settings or ascribed meaning that may be specific to a manufacturer. The following definitions of the terms listed should be applied in interpreting their respective usage throughout this disclosure.

Definitions

Work of Breathing (WOB)—Relates to the energy expended to inhale a breathing gas. It is usually expressed as work per unit volume, for example, joules/liter, or as a work rate (power), such as joules/min. In most instances the term relates to a single breath. In most literature it is measured over several breaths.

Work—It is usually expressed as work joules or it may also be expressed as the work per unit volume, for example, joules/liter.

Power—The rate of work such as joules/min

Equation of Motion for Respiration—Used to describe the pressures exerted by the compliance and resistive forces of the lung.

Selected breath—The stimulator controller intervenes by selecting a breath to stimulate this is done by selecting every other breath in simple ratio of 1:2 up to about a one of every twenty breaths (1:20).

Predecessor breath—The breath immediately prior to a selected breath.

Subsequent breath—The breath immediately after a selected breath.

Companion breath—From the perspective of a selected breath both predecessor breaths and subsequent breaths are defined as companion breaths. In essence all non selected breaths are companion breaths with the immediately following and preceding breaths given unique names.

Pressure control modality—A mode of mechanical ventilation alone and a variable within other modes of mechanical ventilation. Pressure control is used to regulate pressures applied during mechanical ventilation. During Pressure Control Ventilation, the control parameter is pressure and flow is adjusted to reach the specified pressure.

Flow control modality—Used in Volume Control Ventilation. Various flow control modes may be used such as square wave or descending ramp. During Volume Control Ventilation, the control parameter is flow and pressure is a resultant parameter.

Synchronized intermittent mechanical ventilation (SIMV)—A variation of Intermittent Mechanical Ventilation (IMV), in which the ventilator breaths are synchronized with patient inspiratory effort if the patient is making an effort to inspire. The breath mode is most often a mandatory breath mode paired with a spontaneous breath mode.

SIMV (Volume Control, PSV)—In this SIMV case the mandatory or assist mode of ventilation is a Volume Control breath with a spontaneous mode of Pressure Support Ventilation.

SIMV (Pressure Control, PSV)—In this SIMV case the mandatory or assist mode of ventilation is a Pressure Control breath with a spontaneous mode of Pressure Support Ventilation.

Bi-level Ventilation—Bilevel positive airway pressure (BPAP), commonly referred to by the trademarked names BiPAP and BiPAP, is a form of non-invasive mechanical pressure support ventilation that uses a time-cycled or flow-cycled change between two different applied levels of positive airway pressure.

PEEP—Positive end-expiratory pressure (PEEP) is the pressure in the lungs (alveolar pressure) above atmospheric pressure (the pressure outside of the body) that exists at the end of expiration.

Mandatory Breath—A breath for which either the timing or size is controlled by a ventilator; the machine initiates (i.e., triggers) and terminates (i.e., cycles) the breath.

Mandatory Breath Period—the time between the beginning of one mandatory breath and the beginning of another mandatory breath. It is calculated in seconds as (60 seconds/ventilator set mandatory breath rate).

Spontaneous Breath—During mechanical ventilation, a breath for which both the timing and the size are controlled by the patient (i.e., the breath is both initiated [triggered] and terminated [cycled] by the patient).

Assist Breath—A breath where the patient initiates a breath but the ventilator terminates it. An assist breath occurs when a mandatory mode of ventilation has been set on the ventilator and the patient exceeds the mandatory breath rate set and the ventilator delivers a mandatory breath in synchrony with the patient demand for a breath.

Turning now to the figures, in FIG. 1a an embodiment of the PEPNS system 100 is shown in a typical environment of use. As is shown, the PEPNS system 100 includes an operating console or stimulator/controller (S/C) 101 which is in communication with an instrumented wye sensor 102 and an electrical stimulation lead assembly 103.

In order to stimulate the diaphragm 104 of a patient 105 the lead system 16 must be properly positioned percutaneously in the neck 106 of a patient 105. Current from the lead system electrically stimulates the phrenic nerve. To monitor the patient and determine that the level of stimulation is in fact sufficient to move the patients diaphragm 104 in the manner desired, the instrumented wye sensor 106 is placed in the breathing circuit tubing 107 of the mechanical ventilator 108 (MV) and measurements carried out by the S/C 101.

The instrumented wye sensor 106 is pneumatically connected to the MV tube circuit 107 to measure both flow and pressure in the wye 114 using standard differential and gauge pressure sensors within the desired range of operation. The wye sensor 106 is electrically coupled to the stimulator/controller 101 via the cable 113. There are a number of other connection methods for sensors for measuring wye flow and pressure. The stimulator/controller 101 has processor or CPU 109 and an integrated pulse generator 110 to supply an electrical output delivered to the lead system 103 via a lead cable 111.

Data received from the wye sensor 106 and lead system 103, as well as the output parameters of the pulse generator 110 are displayed on a display or graphical user interface (GUI) 112 of the stimulator/controller 101. The GUI 112 may be a separate unit or device, such as a monitor, or maybe a dedicated component of the stimulator/controller 101. It will likely have both a touch screen for entering information and a high-resolution display for displaying various information to the user. Software is used to program the CPU to perform the desired tasks of reading inputs, performing algorithmic calculations and setting outputs based upon the user set inputs and algorithmic calculations.

Figure 1B:
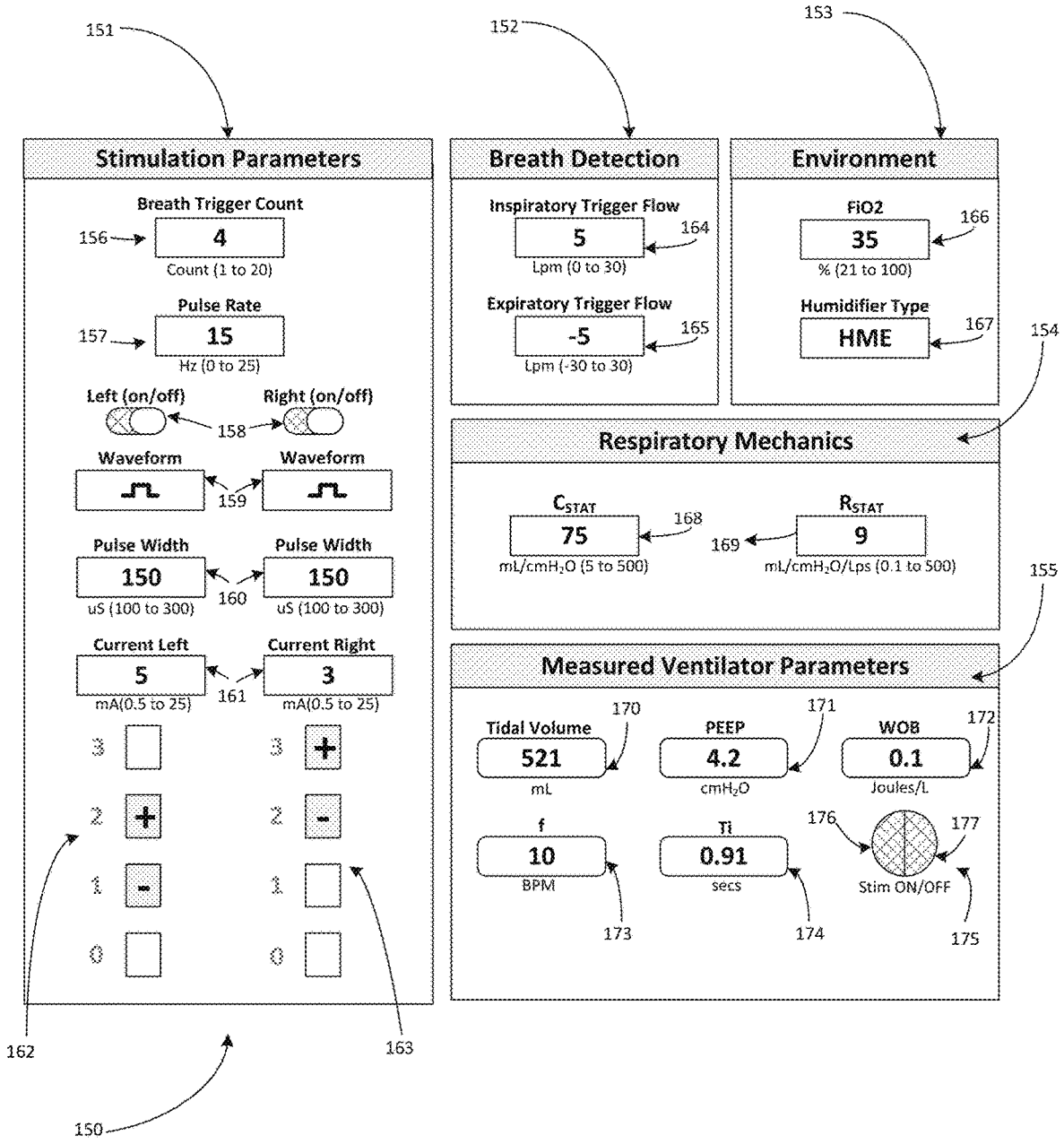
FIG. 1b is a diagram of the one most common user settings inputs and measurement outputs from the PEPNS System graphical user interface.
Figure 2:
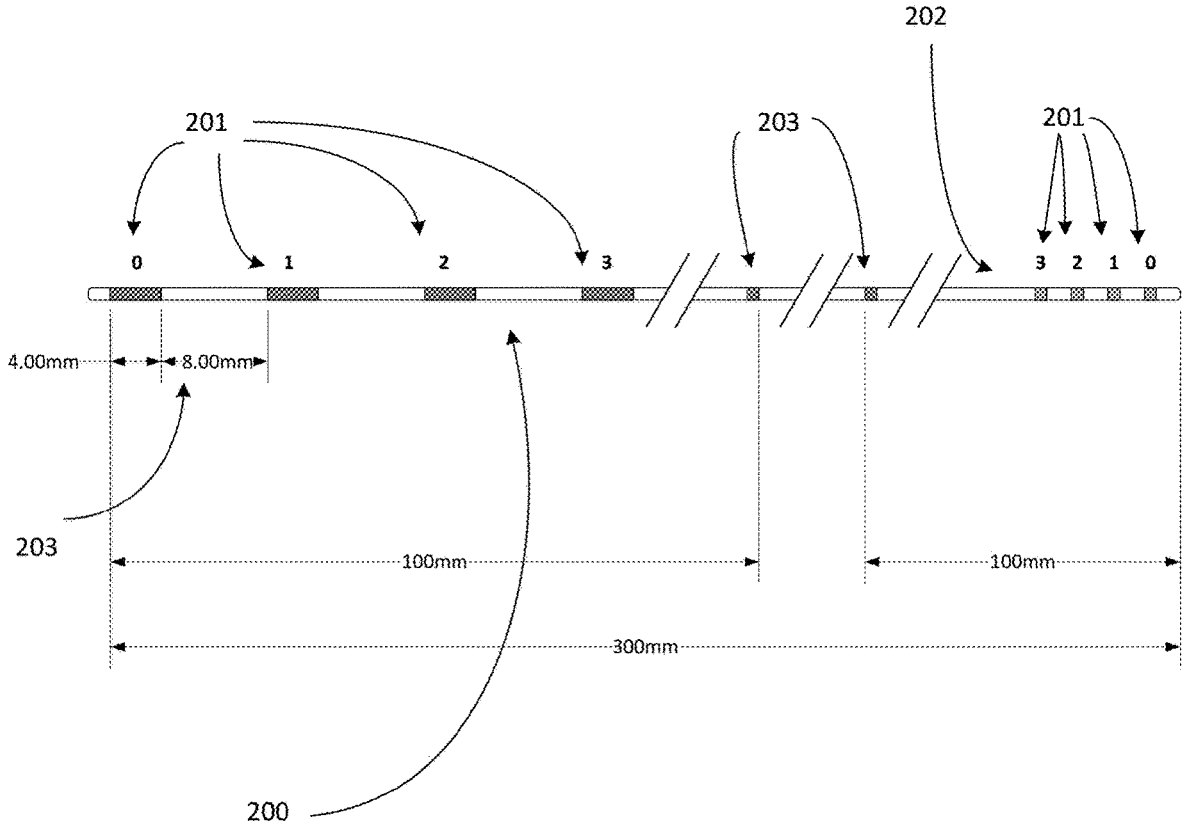
FIG. 2 is a drawing of the PEPNS Lead showing electrodes and contacts.

FIG. 1b shows a simplified graphical user interface for the PEPNS stimulator/controller in terms of user inputs and measurements outputs. It shows a single display 150 of the GUI divided into 5 sub-sections Stimulation Parameters 151, Breath Detection 152, Environment 153, Respiratory Mechanics 154 and Measured Ventilator Parameters 155. There can be multiple displays for showing graphs similar to FIG. 4, alarm logs etc. which are not shown directly here but are known in the design of user interfaces for medical devices. The CPU reads the GUI 150 inputs and makes the appropriate hardware settings under software and hardware control. The Stimulation Parameters are set according to the Breath Trigger Count 156 which dictates the count at which breaths are stimulated between 1 and 20. The stimulation Pulse Rate 157 which dictates the frequency in Hz of pulses delivered during a breath. The display 150 also displays the units under each settings box and the potential range possible for the setting.

The PEPNS console may stimulate up to two separate leads denoted left and right 158 on the GUI. A switch is provided for both the left and right leads to enable or disable stimulate on one or both leads. The type of waveform 159 in terms of the current profile use for stimulation is also settable. This waveform is used to control how current is delivered and changes over time during a single breath. For the disclosure shown a square wave 159 has been shown which means the stimulation current remains constant over the entire inspiratory breath. Electrical stimulation is only delivered during designated inspirations dictated by the Breath Trigger Count 156. It is also possible to select ramped, sinusoidal or other combinations of current waveform using the controls 159 for the left and right leads which allows adjustment according to the chosen waveform over the entire breath. In the case of a ramped waveform selection and initial current and end current would need to be set along with a ramp current. This the GUI 150 would automatically modify to accommodate the necessary settings based upon the waveform selected. This allows the clinician to adjust the rate of diaphragm contraction and make the breath similar to that of a person breathing normally.

Given that it is possible to stimulate both the left and right phrenic nerves with separate stimulation leads duplicate settings are given to enable the clinician individual lead adjustment. The pulse width of the electrical pulse is also selectable 160 with different types of balanced and unbalanced biphasic pulse selections possible not shown in this settings window. The individual current setting for both the left and right leads 161 are adjustable. Since the lead is supplied with 4 electrodes, the user is able to select which electrodes they would like to stimulate and by depressing the electrode icons shown in 163 and 162 select the polarity of the electrode. In the case shown only two electrodes are stimulateable electrically and one of the electrodes must be positive while the other is negative. Other combinations are also possible as well such as two electrodes being negative and two being positive. The breath detection section 152 is used to allow the PEPNS System to detect when inspiration and exhalation is occurring. The Inspiratory Trigger Setting 164 is used to detect the onset of patient or ventilator inspiration. And the Expiratory Trigger Setting 165 is used to detect the onset of expiration. The expiratory trigger setting is capable of being set both positive and negative to enable the clinician to enable stimulation during plateaus if so desired. During a plateau the exhaled flow is temporarily delayed resulting in a inspired flow waveform that is close to 0 Lpm for the plateau period before switching to exhalation.

The environment section 153 is used to inform the PEPNS System of what the ventilator FIO2 166 is set to and the type of humidification used by the ventilator. These environmental settings will improve the accuracy of the flow measurement by the PEPNS System the PEPNS system to more accurately correct for delivered gas conditions in terms of density, viscosity and humidity. The Respiratory Mechanics section 154 is where the clinician is able to input the patient static lung compliance 168 and resistance 169. The Measured Ventilator Parameters 155 allows the user to assess how well the PEPNS System is operating in terms of trigger sensitivity and measured volume accuracy. The inspired tidal volume 170 is shown in mL which is calculated by integrating the wye flow over the inspiratory period. PEEP 171 (Positive End Expiratory Pressure) is the pressure measured in cmH2O at the end of inspiration. The breaths per minute f, 173 is measured using the time calculated between successive inspirations averaged over a number of breaths. Ti 174 inspiratory time is calculated as the time between the detection of inspiration and the detection of exhalation. Each time stimulation is performed during an inspiration the Stim on/off light 175 is highlighted denoting to the user that electrical stimulation is active during that specific breath. Both the left and right slide buttons 158 need to be turned on for electrical stimulation to occur on both the left and right lead.

In order to highlight that only one side is stimulating the specific left 176 or right side 177 of the light may be lit. If a left or right stimulation is disabled the settings related to the left or right side may be faded denoting the specific side that is disabled.

A number of different implementation are possible and the description above is for illustration purposes only. For instance, in one implementation the Breath Trigger Count is set to four then every fourth breath is stimulated. Or the rate at which breaths are stimulated could be implemented at random breath count interval which averaged to the set breath trigger count averaged over a number of breaths to matched the set breath trigger count and achieved the same desired effect. This would have the benefit of making it difficult for an alert patient to determine when the next electrical stimulation breath would occur. In general, the device will select one breath from many for intervention based upon the user setting.

Turning now to the lead system 103, as mentioned above the lead system 103 comprises a unitary lead body having a distal end with at least four electrodes and a proximal end having a set of four terminals for connection to the S/C. In the embodiment shown in FIG. 2, the lead 200 is a multipolar lead having at least four electrodes 201 (0-3) contained within a lead body 202. Each electrode is in communication with the stimulator/controller 101 (see FIG. 1) via lead cable 103 (see FIG. 1). By providing each lead 201 (0-3) with multiple electrodes (or poles) 201 ensures that at least one pair of electrodes will lie close to and cross the phrenic nerve 115 or 116 which from here on will be referred to as traverse to the nerve in the manner shown in FIG. 1 at all times after the lead is inserted or subsequently repositioned due to neck motion or repositioning of the patient (patients are routinely repositioning in the ICU to prevent bedsores).

By placing the lead or leads 103 transverse to the nerve 115 or 116 a pair of stimulation poles 201 can be selected to recapture the nerve 115 or 116 if necessary without requiring further physical manipulation of the lead 103 after insertion, thereby reducing the potential for infection and improving device usability. Put another way: the spacing of electrodes 203 along the lead 202 ensures that electrical communication between the lead 202 and the phrenic nerve 115 or 116 is maintained by allowing any of the four-pole to be energized. Four poles were chosen based upon minimizing cost and complexity of the electronics but the design will also work just as well with 5, 6, 7 etc. poles. Thus, even if the position of the lead 202 has shifted as a result of patient movement or other factors two of the four poles 201 will always be in sufficient proximity to the phrenic nerve 115 or 116 to allow for stimulation to occur. Any combination of leads, surface area, distance between electrodes and lead diameter can be envisage that would optimize the stimulation ability of the lead to excite the phrenic nerve.

It is expected that a single pair of electrode sites closest to the phrenic nerve that best stimulate the nerve in terms of WOB may be found experimentally or by an automated search algorithm by the clinician in each instance. Both unipolar and bipolar stimulation regimes are contemplated with both anodal and cathode stimulation available for the therapeutic use. Both monophasic and balanced and unbalanced biphasic current stimulation are contemplated but it is expected that biphasic stimulation from a single pair of well-placed electrode poles will be optimal and result optimal WOB.

Figure 3:
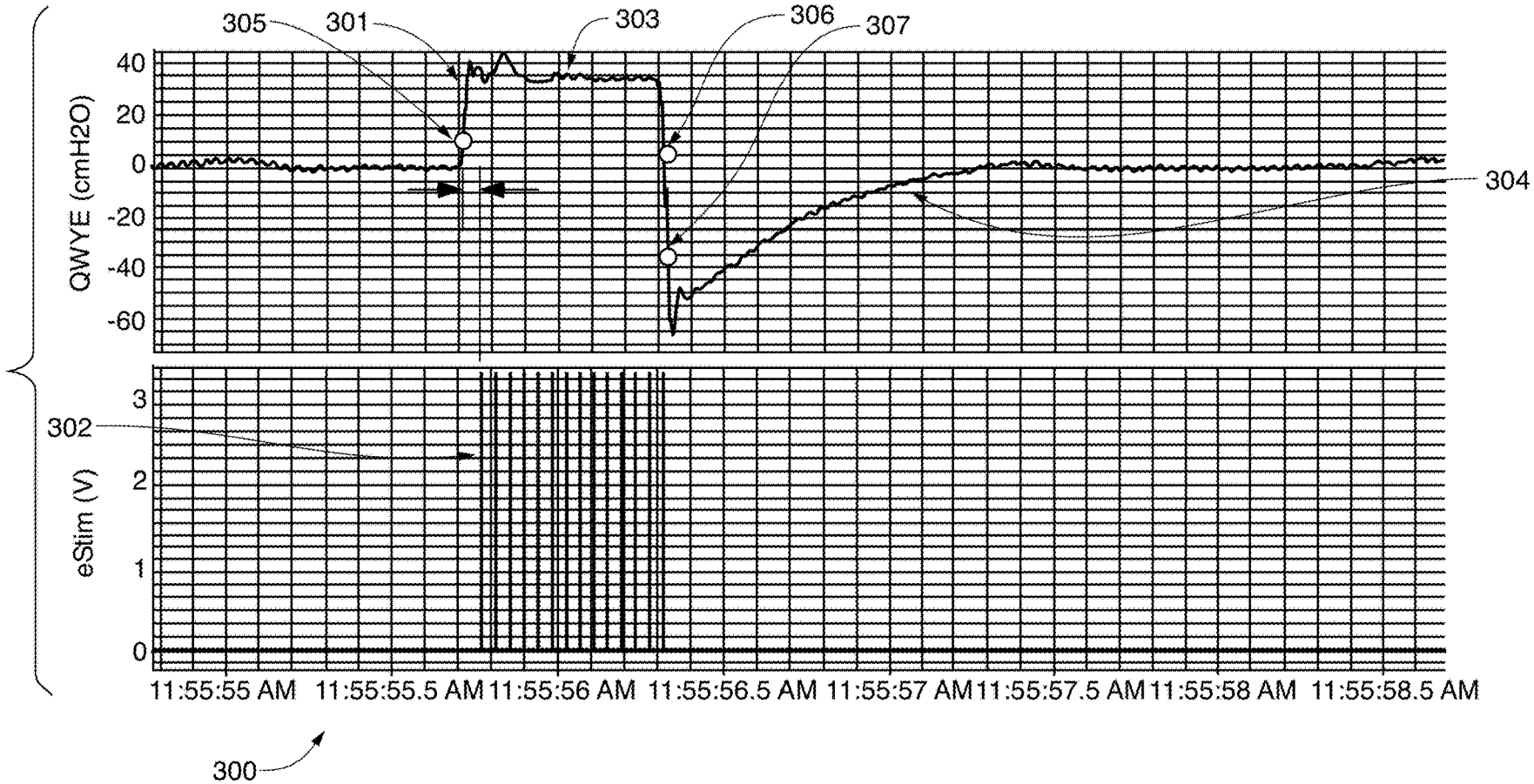
FIG. 3 is a graph of wye flow showing the potential inspiratory and expiratory triggering flow settings for a single breath along with the requests for electrical stimulus.

FIG. 3 shows a graph 300 of the wye flow 301 and electrical stimulation signal 302 for a single inspiratory and expiratory phase of a breath. The human breath has an inspiratory phase 303 characterized by a positive flow of air through the wye into the patient, and an exhalation phase which begins when wye flow drops below zero 304 and turns negative as the patient exhales the volume just inspired defined by convention. This end of inspiration event typically begins the outflow portion of the breath cycle. In operation, the stimulator will deliver the electrical stimulation 302 starting with the inspiratory phase when flow exceeds a predetermined level 305 and end stimulation at the start of the exhalation phase when flow drops below a predetermined level 306 to 307, thus stimulus will occur only during the selected breath. Since the stimulation is not continuous for each inspiration there will typically be a predecessor mechanical ventilator breath and a subsequent breath. Electrical stimulation pulses are delivered at the set pulse rate within the designated breath. The selection of the designated stimulation breath count may be a simple ratio. That is selected breaths may occur every other breath (1:2) to any arbitrary value say one selected breath every 20 breaths (1:20). It is expected that a ratio of 1:4 or so will provide adequate treatment for VIDD however this will need to selected based upon clinical practice.

It is also envisaged that the rate at which breaths are stimulated may also be implemented as or a random breath count interval which would ensure the average matched the set breath count rate and achieved the same desired effect. This would have the benefit of making it difficult for an alert patient of determine when the next electrical stimulation breath would occur. In general, the device will select one breath from many for intervention.

Figure 4:
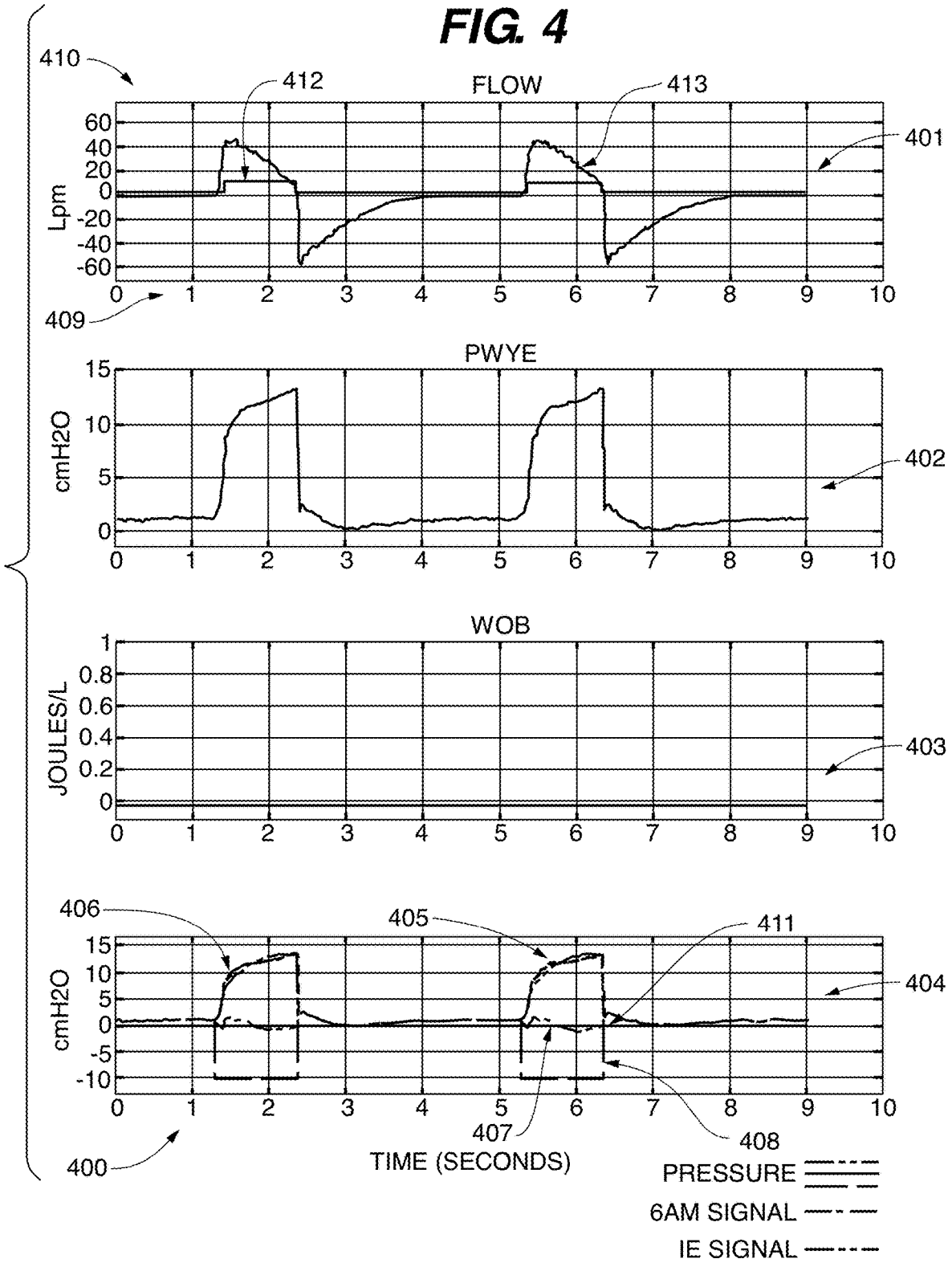
FIG. 4 is a graph of PCV (Pressure Control Ventilation) trace delivered by the PB840 ventilator with Pi=14 cmH2O, Ti 1.08 seconds, f=15 bpm, % Rise Time=15%, PEEP 0 cmH2O, CSTAT=44 ml/cmH2O, RSTAT=7 cmH2O/Lps. The breaths shown do not have any patient effort and are mandatory.
Figure 5:
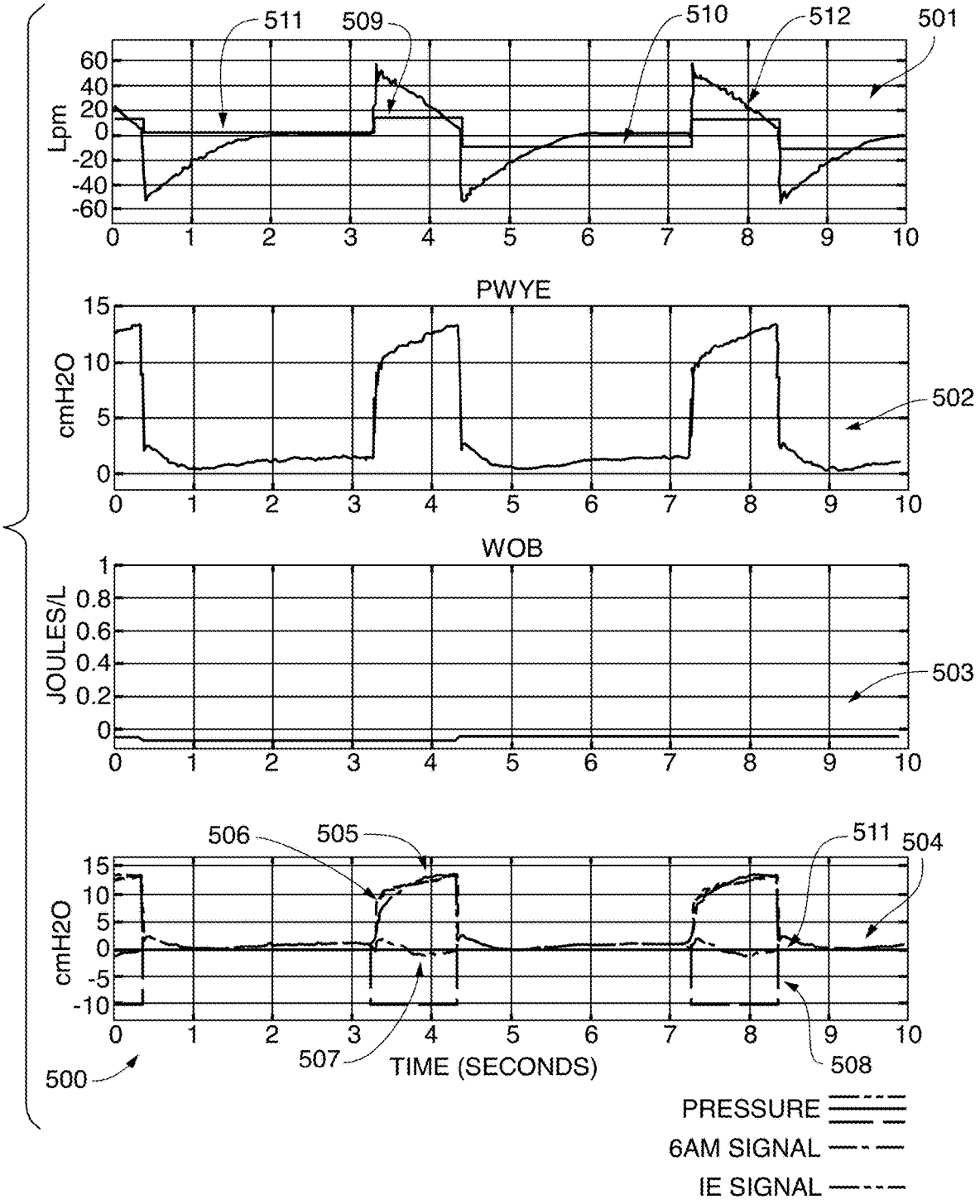
FIG. 5 is a graph of VCV (Volume Control ventilation) trace delivered by the PB840 ventilator with Vt=530 ml, Flow max=50 Lpm, Ti 1.16 seconds, f=15 bpm, PEEP 0 cmH2O, CSTAT=44 ml/cmH2O, RSTAT=7 cmH2O/Lps. The breaths shown do not have any patient effort and are mandatory.

FIG. 4 and FIG. 5 illustrate the difficulty in distinguishing between different ventilator breath types and also show a way of displaying waveforms to the clinician that aid in communicating the effect of electrical stimulation has on the breath cycle of the patient. This additional graph screen may be available within the settings window or as a separate window on the GUI. At the basic level in a ventilator, breaths are either flow controlled or pressure controlled, in some modes it is a combination of both. FIG. 4 show a PCV breath and FIG. 5 shows a VCV breath and when compared look nearly identical. Both FIGS. 4 and 5 displays four windows with a number of traces in each window ranging from one to five. The dimensional units are displayed at the side of each window on the Y-axis 410 versus time in seconds on the X-axis 409 as shown in FIG. 4. Thus, distinguishing between these fundamentally different types of breaths based solely on the flow and pressure traces is a near impossible task in certain cases. Both traces show a mandatory breath mode of ventilation. The trace names are the same in FIG. 4 and FIG. 5.

FIG. 4 graphs 400 were generated using PCV (Pressure Control Ventilation) using the PB840 ventilator with Pi=14 cmH2O, Ti 1.08 seconds, f=15 bpm, rise time=15%, PEEP 0 cmH2O. The simulation lung was set to $C_{STAT}$=44 ml/cmH2O, $R_{STAT}$=7 cmH2O/Lps.

The graph 400 displays the following traces plotted over time:

- Graph window 401 shows Measured Wye flow 413 in Lpm and the Inspiratory and Expiratory Trigger flow in Lpm. In this case the inspiratory trigger flow is 10 Lpm and the expiratory trigger flow is 0 Lpm.
- Graph window 402 shows Measured Wye pressure in cmH2O.
- Graph window 403 shows WOB in Joules/L.
- Graph window 404 shows Predicted Wye pressure in cmH2O 405, the Measured Wye pressure 406 which is the same as 402, the difference in pressure between the wye and predicted pressure 407, the inspiratory period 408 and the electrical stimulation signal 411.

FIG. 5 graphs 500 were generated using VCV (Volume Control ventilation) on PB840 ventilator with Vt=530 ml, Flow max=50 Lpm, Ti 1.16 seconds, f=15 bpm, PEEP 0 cmH2O. The simulation lung was set to $C_{STAT}$=44 ml/cmH2O, $R_{STAT}$=7 cmH2O/Lps.

The graph 500 displays the following traces plotted over time:

- Graph window 501: Measured Wye flow 512 in Lpm and the Inspiratory and Expiratory Trigger flow in Lpm. In this case the inspiratory trigger flow 509 is 10 Lpm and the expiratory trigger flow 510 is −10 Lpm. The preceding breath shows that the Expiratory trigger flow 511 had been 0 Lpm but was changed to −10 Lpm.
- Graph window 502: Measured Wye pressure in cmH2O.
- Graph window 503: WOB in Joules/L.
- Graph window 504: Predicted Wye pressure in cmH2O 505, the Measured Wye pressure 506 which is the same as 502, the difference in pressure between the wye and predicted pressure 507 and the inspiratory period 508.

The advantage of showing the trigger flow rate on the Graph Window 501 in relation to the measured flow rate 512 is the clinician is able to see the effect of the inspiratory and expiratory triggering flow rates visually on the flow graph and see the effect it has on delaying triggering for both inspiration 509 and exhalation 511 and 510.

The calculation of the predicted wye pressure as a function of the equation of motion and subsequent calculation of the work of breathing (WOB) has been outlined in U.S. Pat. No. 9,682,235. The differences between the VCV and PCV breaths will only become evident when the patient is actively breathing and the volume-controlled breath shows pressure droop whereas the pressure-controlled breath will increase the delivered flow to respond to the increased patient demand. Similarly, it is also difficult to discern the difference between a pressure support breath and a pressure control breath if the inspiratory time is relatively constant. Electrically stimulating a patient's diaphragm when the patient is already initiating an assist or spontaneous breath may not be desirable in cases where the patient becomes agitated by the sensation electrical stimulation.

The work of breathing measurement is derived based upon the respiratory equation of motion. Although unnecessary for a qualitative indication of work or power it is best to convert measurements to a uniform standard and the patient work level or power expended in a breath is reported as the Work-of Breathing (WOB). This convention reduces the necessity to convert units and makes direct comparison with normal levels of WOB possible. The ventilator may be used to assess the patient's compliance and resistance because it dictates when static respiratory mechanics maneuvers can be initiated and performed. The resultant measured static compliance and resistance measurement values will then be used to determine the WOB for the patient. The user will need to transfer the ventilator measured compliance and resistance measurements manually from the ventilator to the PEPNS console. It will be necessary to perform respiratory mechanics periodically because the patient respiratory mechanics may change as ventilation progresses.

In theory if the patient does not make a voluntary inspiratory effort during a mandatory breath or the PEPNS System does not electrically stimulate the diaphragm, the WOB should be very close zero joules/L within the tolerance of the accuracy of the measurements being made. Work is normally measured in Joules but dividing by the volume allows the level of work to be normalized against a unit volume. The equation of motion equation should predict the wye pressure accurately and when the measured wye pressure matches the predicted wye pressure it indicates that there is no patient effort and thus no WOB. A difference will occur in the predicted and measured wye when the diaphragm is stimulated and these will be attributed to diaphragm effort.

The benefit of this approach is that the WOB can be assessed in relation to the level of work a normal healthy patient exerts during breathing at rest. Normal WOB has been reported in the literature by Levy in 1995 to be 0.3 to 0.5 J/L in healthy children, adolescents, and young adults. Brochard in 2012 reported normal WOB values range from Normal WOB values range between 0.2 and 1 J/L. Certain disease states that increase lung resistance and compliance dramatically increase the level of work a patient has to exert to breath.

Figure 6:
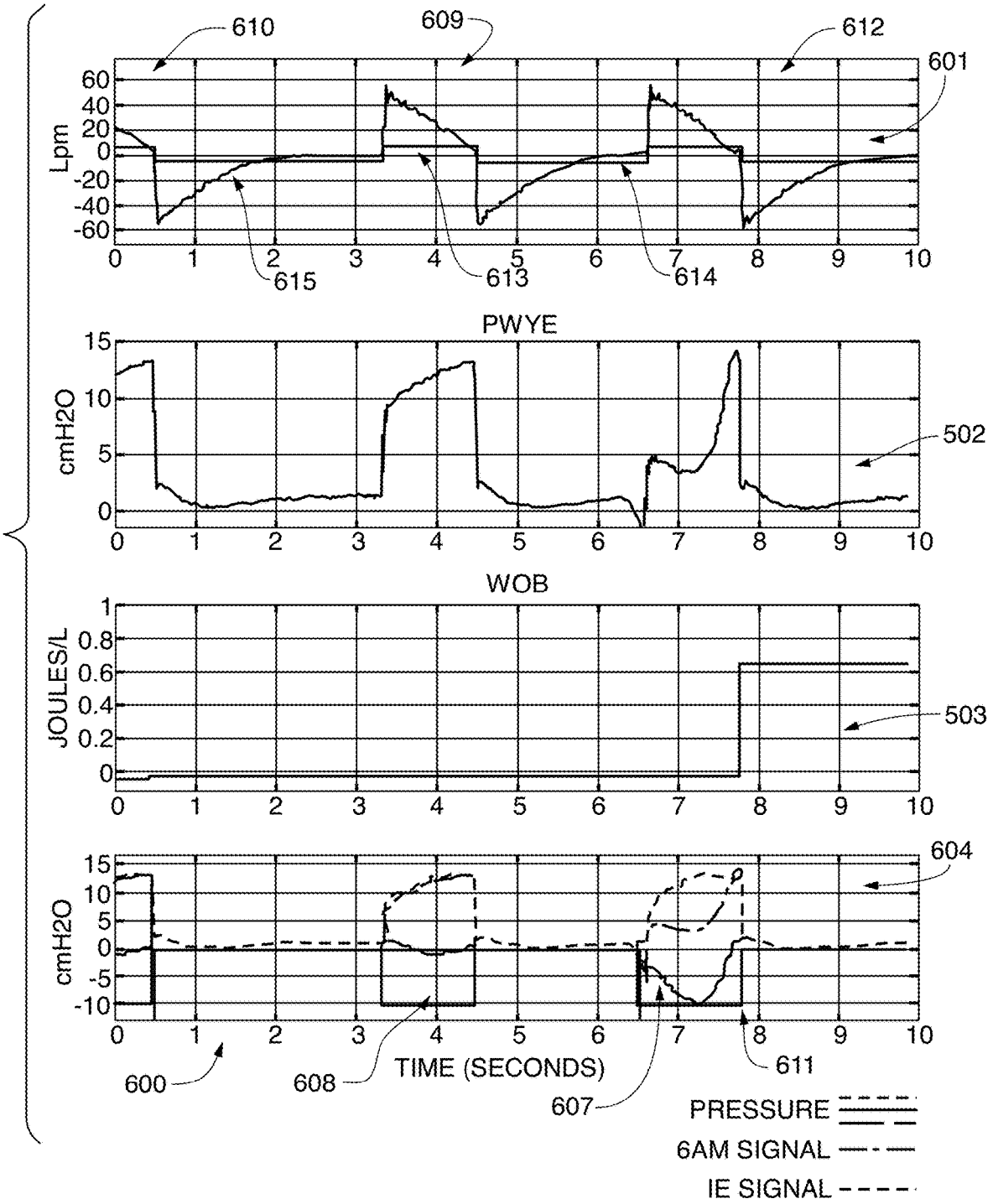
FIG. 6 is a graph of a VCV (Volume Control ventilation) delivered by the PB840 ventilator with Vt=530 ml, Flow max=50 Lpm, Ti 1.16 seconds, f=15 bpm, PEEP 0 cmH2O, CSTAT=44 ml/cmH2O, RSTAT=7 cmH2O/Lps. The first two breaths are mandatory but the 3rd breath is a patient-initiated assist breath.

FIG. 6 graphs 600 were generated using VCV (Volume Control Ventilation) on PB840 ventilator with Vt=530 ml, Flow max=50 Lpm, Ti 1.16 seconds, f=15 bpm, PEEP 0 cmH2O. The simulation lung was set to $C_{STAT}$=44 ml/cmH2O, $R_{STAT}$=7 cmH2O/Lps.

The graph 600 displays the following traces plotted over time:

Graph window 601: Measured Wye flow in Lpm 615 Along with the inspiratory and expiratory trigger flows 613 and 614 respectively.

Graph window 602: Measured Wye pressure in cmH2O

Graph window 603: WOB in Joules/L.

Graph window 604: Predicted Wye pressure in cmH2O 605, the Measured Wye pressure 606 which is the same as trace 602, the difference in pressure between the measured wye and predicted pressure 607 and the inspiratory period 608. Electrical stimulation was enabled for this breath and the trace denoting the implementation of stimulus on this breath is shown as 611.

The PEPNS console to be able to detect that the patient is taking breaths of their own volition and to give the operator on the PEPNS System the ability to cease electrical stimulation during these patients-initiated breaths. This prevention of electrical stimulation requirement may be based upon the measured WOB during these breaths. The WOB is measured for all breaths and if it's not within the range of to 0.0+/−0.1 joules/L, then it means the patient is also actively breathing. The allowable tolerance for the minimum WOB could be set by the clinician to a minimum level of WOB that the clinician is interested in identifying. For instance, if the patient is performing work but not in their opinion sufficient to prevent diaphragm atrophy or they are only performing work at the start of the breath it may be desirable to force the patients diaphragm to perform work throughout the breath cycle to exercise the diaphragm during a larger range of motion.

Typically, electrical stimulation will be initiated when the patient is unable to breath spontaneously on the ventilator and the patient is ventilating on a mandatory mode of ventilation as shown in FIGS. 4 and 5. In order to prevent delivering stimulation with assist and spontaneous breaths a minimum breath rate may be entered into the PEPNS console. This ventilator set breath rate can be used to calculate the maximum time period between breaths or it could be entered directly as a setting. With this knowledge, the PEPNS System can assess if a ventilator breath has not occurred before this time period has exceeded, a mandatory breath will be delivered by the ventilator. Thus, if the ventilator breath rate was set to 10 bpm the maximum time between breaths shown in FIG. 4.0 would be 6 seconds. If the breath rate was detected to be 10 bpm then the PEPNS system would know that the patient is being delivered mandatory breaths only assuming it knew this was the minimum breath rate. The advantage of this scheme is that no communication I needed between the ventilator and the PEPNS System other than the clinician informing the PEPNS System via the GUI of the ventilator mandatory breath rate.

Figure 7:
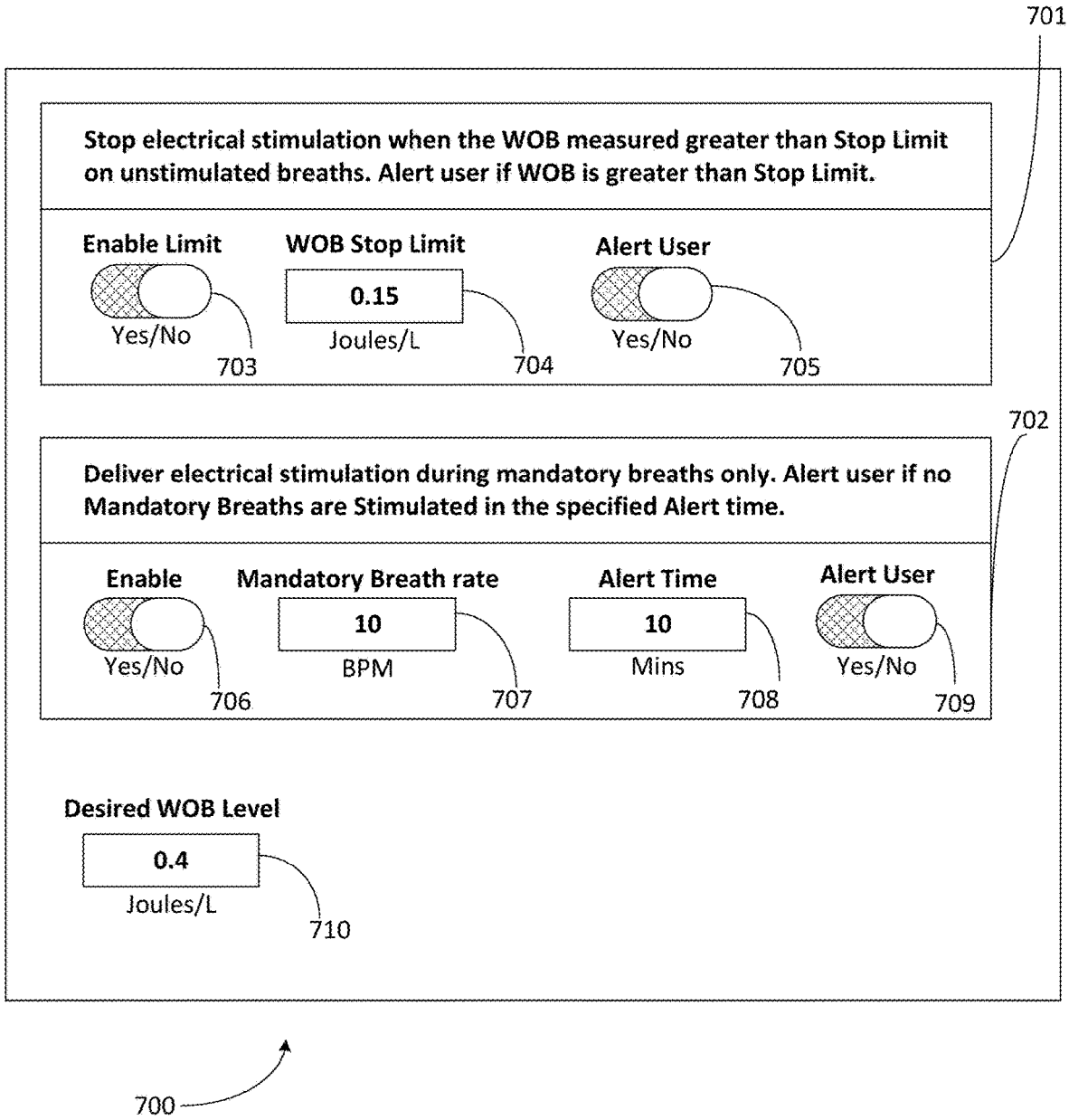
FIG. 7 is a drawing of proposed user interface settings related to ceasing electrical stimulation, alerting the user when the patients WOB exceeds specified limits based upon predefined settings of WOB. Settings related to enabling the delivery of electrical stimulus for mandatory breaths only and alerting the clinician to the fact that no mandatory breaths have been delivered with a specified interval.

FIG. 7 shows the potential settings that could be used to implement these features:

1. The PEPNS System cease or desist electrical stimulation when the patient actively takes a breath. Do not perform any electrical stimulation on a patient-initiated breath.
2. Alert the operator when the patient is actively breathing. Generate an alarm bringing the operators attention to the fact that the patient is now initiating breaths.
3. Provide electrical stimulation on mandatory breaths only at the desired breath count rate count on mandatory breaths only.
4. Provide electrical stimulation if the work of breathing (WOB) measured for a particular breath or averaged over a period of time does not reach the desired level on a spontaneous or assist breaths. Unfortunately, it's possible to set a pressure support level in pressure support ventilation (PSV) that will stop the patient from actively breathing on their own.
5. Alert the operator if the WOB level for assist and spontaneous breaths is not being achieved.
6. Deliver electrical stimulus on mandatory breaths only.
7. Continue stimulation independent of any breath type.

The settings window 701 gives the user the ability to stop electrical stimulation 703 when the WOB measured is greater than the WOB Stop Limit 704 for unstimulated breaths. This WOB Stop Limit may be set anywhere between 0.1 and 1.0 Joules/L. The user is also able to select if they want to be alerted if the WOB is greater than Stop Limit 704. The buttons 703 and 705 use a sliding action to enable and disable but are not limited to this implementation.

The settings window 702 gives the user the ability to deliver electrical stimulation via the sliding button 706 during mandatory breaths only. The allowable period of time between breaths is calculated from the user entered Mandatory Breath Rate 707. The mandatory time between inspirations or breaths is calculated as follows:

Time Between Breaths=(60 seconds/Mandatory Breath Rate).

If this period of time elapses between breaths then it means that the breath is a mandatory breath. If the time before the next breath is delivered is shorter than this period then it means that the breath is either a spontaneous or assist breath. The user is able to select via the Alert User button 709 if they want to be made aware that the device is not delivering stimulus to mandatory breaths. The time out period may be selected by adjusting the Alert Time setting 708. In the case shown the setting is in minutes but it could also be implemented as a breath count.

The settings window 700 also gives the user the ability to inform the PEPNS device at what rate the ventilator is set to deliver mandatory breaths. If the clinician has set a mandatory rate of 10 bpm and is breathing at 12 bpm then all breaths will be delivered in assist mode. If the clinician has set SIMV two of the breaths will be delivered with spontaneous modes of ventilation will all others will be delivered in assist mode.

Figure 8:
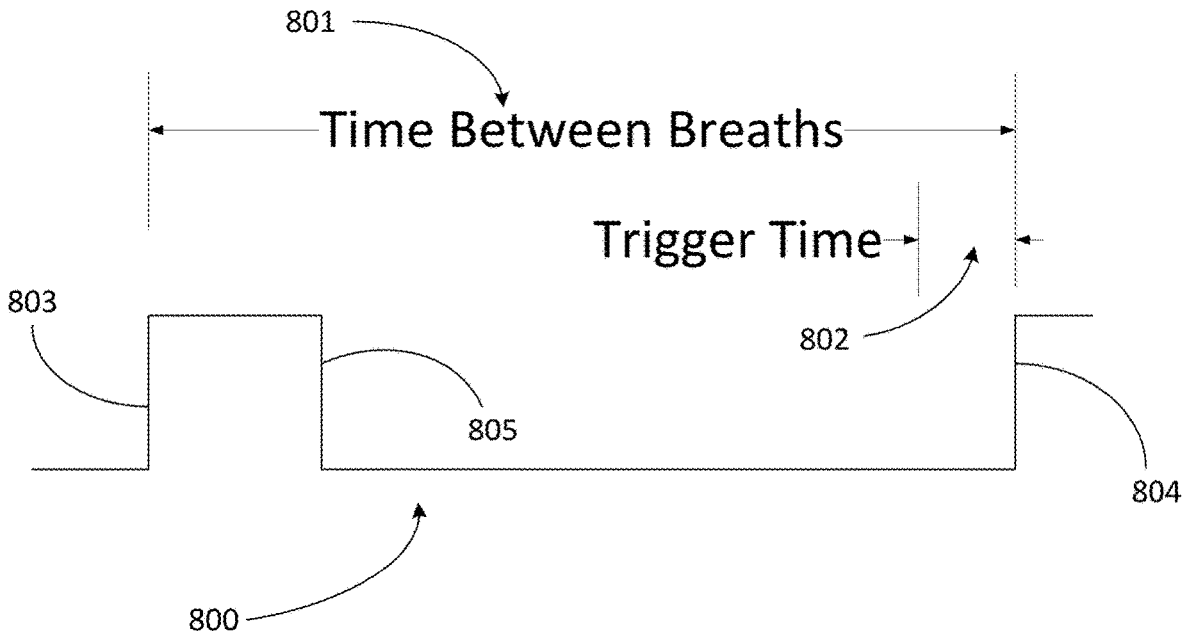
FIG. 8 is a diagram of the implementation for detecting a mandatory breath.

FIG. 8 shows the inspiratory/expiratory phase between breaths 800. These phases are determined by software using the flow sensor to measure flow and based upon the inspiratory and expiratory trigger flows set on the graphical user interface. When the inspiratory flow exceeds the set Inspiratory Trigger Flow inspiration is declared and when the inspired flow drops below the Expired Trigger Flow when in inspiration, exhalation is declared. The mandatory Time Between Breaths 801 may calculated as previously described from the Mandatory Breath Rate 707 (FIG. 7).

The time between breaths may also be automatically measured by the PEPNS system by measuring the time between inspirations 803 and 804. 803 and 804 show the rising edge detection of inspiration and 805 shows the falling edge detection of exhalation from the Inspiratory and Expiratory Trigger flows. A knowledge of the time between mandatory breaths 801 may be used to eliminate any potential lag between a ventilator-initiated breath and the detection of a breath i.e. the Trigger Time 802 by the PEPNS console by initiating electrical stimulation. This Trigger Time may be a predefined period just before the time before the breath period expires, say for instance somewhere between 50 to 300 msecs before the ventilator would deliver its mandatory breath. If electrical stimulation is initiated before the time between breaths elapses then there will be no lag in detection of inspiration. The determination of the time between breaths may be measured by the CPU and software by integrating the time between the breaths to simply determine if a breath is mandatory or not, based upon the set mandatory ventilator breath rate.

Another way to independently assess if the ventilator is delivering mandatory breaths is to examine the variance in the time between breaths over a number of breaths. If the breath rate is constant and the standard deviation of the time is very small and within the allowed variance of breath rate detection then the patient can only be delivered mandatory breaths. If the variance in the time between breaths exceeds 100 msecs for instance then it's clear that the patient is also triggering breaths. Testing has shown that that the variance in time between mandatory breaths with the PEPNS system is less than 50 msecs. To be clear the variance in breath detection is a function of how accurately a breath period or inspiratory time may be detected and the sample rate of software. Testing has shown that these detection accuracies are much less than 50 msecs but they are a function to some extent of the triggering flow rates.

The WOB may also be assessed for unstimulated breaths. If the average WOB is below a desired WOB level 710 FIG. 7 then electrical stimulation may be allowed on breaths other than mandatory breaths.

The inspiratory time period is measured by the PEPNS System. If the inspiratory time period is constant within the allowed variance of inspiratory time period detection then the patient is being delivered only mandatory breaths.

Setting a maximum time period between breaths or a minimum breath rate similar to an apnea period on the PEPNS Console will have a number of advantages that can be exploited by the PEPNS System to enhance patients' safety:

1. If the measured breath rate exceeds the set breath rate then the patient is initiating breaths which may be a sign that the patient is waking up or is agitated. The detection of this event may be used to alert the operator that the patient is no longer passive and to make any changes necessary.
2. Preceding the ventilator-initiated breath with electrical stimulation eliminates any lag between the PEPNS system detecting a breath and initiating electrical stimulation. Detecting that a breath has occurred within the trigger time period lets the PEPNS system know that electrical stimulation is functional.
3. Using such a predefined time between breaths allows the system to avoid electrical stimulation during assist and spontaneous breaths. If a breath occurs before this time has elapsed then the PEPNS console could avoid counting this breath if the operator desired to prevent stimulation during spontaneous or assist breaths. Thus, when the patient begins to awake and start to breath in assist mode or spontaneously, the PEPNS System will inherently recognize the occurrence of these breaths and avoid electrical stimulation when the patient is already creating their own WOB.
4. The PEPNS System may assess the WOB over a number of assist or spontaneous breaths to determine if electrical stimulation should be used based upon not meeting a minimum level of WOB.

Once a patient begins to breath spontaneously it may not be possible to set the support level on the ventilator to achieve the desired WOB. This can be assessed with the aid of the WOB measurements provided by the PEPNS system. The same if potentially true for a pressure control mandatory mode of ventilation as assist breaths.

The human body is highly efficient and will only perform work if necessary. Setting a pressure support level to provide sufficient volume without stopping the patient from doing work is extremely difficult and has spawned breath modes such a NAVA (Neurally adjusted ventilatory assist) that enable the clinician to determine the specific support level to set. One of the difficulties in maintaining such support levels is the patient's condition is ever changing and what works for 1 hr may not work for 24 or 48 hrs. This is one of the benefits of electrical stimulation and the patient can be forced to perform diaphragm work independent of the ventilator settings and how much over or under support is available to the patient.

In addition to the above, the following literature references are incorporated herein by reference in their entirety:

Levy M M, Miyasaki A, Langston D. Work of breathing as a weaning parameter in mechanically ventilated patients. Chest. 1995 October; 108(4):1018-20. PubMed PMID: 7555112.

Brochard L, Martin G S, Blanch L, Pelosi P, Belda F J, Jubran A, Gattinoni L, Mancebo J, Ranieri V M, Richard J C, Gommers D, Vieillard-Baron A, Pesenti A, Jaber S, Stenqvist O, Vincent J L. Clinical review: Respiratory monitoring in the ICU—a consensus of 16. Crit Care. 2012 Dec. 12; 16(2):219. doi: 10.1186/cc11146. PubMed PMID: 22546221; PubMed Central PMCID: PMC3681336.

The many features and advantages of the invention are apparent from the above description. Numerous modifications and variations will readily occur to those skilled in the art. Since such modifications are possible, the invention is not to be limited to the exact construction and operation illustrated and described. Rather, the present invention should be limited only by the following claims.

What is claimed is:

1. An apparatus comprising:

a lead system;

a stimulator circuit configured to deliver electrical stimulus via the lead system; and a controller circuit in operative communication with the lead system and stimulator, the controller circuit being configured and arranged to using a flow sensor, detect inspiration and expiration of a patient exceeding a set trigger flow, calculate time between the inspirations that exceed the set trigger flow, and control the stimulator circuit for delivering the electrical stimulus via the lead system in response to the time that passes after one of the inspirations exceeding the set trigger flow, and before a subsequent inspiration that exceeds the set trigger flow, exceeding a set time.

2. A percutaneous electrical phrenic nerve stimulation system comprising:

a lead system;

a stimulator configured to deliver electrical stimulus via the lead system; and a controller circuit in operative communication with the lead system and stimulator, the controller circuit being configured to calculate work of breathing (WOB) for patient breaths detected by a flow sensor based on lung compliance and resistance of the patient, and the controller circuit being configured to:

control the stimulator to deliver the electrical stimulus when the WOB is less than a predetermined level; *and cease the delivery of electrical stimulation from the stimulator when the WOB meets or exceeds the predetermined level.*

3. A percutaneous electrical phrenic nerve stimulation system comprising:

a lead system in electrical communication with a stimulator;

a controller circuit in operative communication with the lead system and stimulator; and a GUI in operative communication with the controller circuit, the controller circuit being configured to calculate work of breathing (WOB) for patient breaths detected via a flow sensor, including assist breaths and spontaneous breaths based on lung compliance and resistance of the patient, and the stimulator configured to deliver electrical stimulus via the lead system, the controller configured to cease the delivery of electrical stimulation from the stimulator if the assist breath WOB and spontaneous breath WOB are above a desired level of WOB.

4. The apparatus of claim 1, wherein the controller circuit includes:

a pulse generator configured and arranged to control the stimulator for delivering the electrical stimulus by supplying electrical pulses to the lead system based on the inspiration and expiration and the set time between inspirations; and a processor circuit configured and arranged to provide the set time between inspirations that is used in supplying the electrical pulses from the pulse generator.

5. The apparatus of claim 4, wherein the processor circuit is configured and arranged to generate an output for communicating characteristics of the sensed inspiration and expiration, and for communicating characteristics of the stimulation.

6. The apparatus of claim 5, wherein the output includes a graphical output that displays characteristics of one or more of: the electrical pulses generated by the pulse generator, the sensed inspiration and expiration, and the stimulation.

7. The apparatus of claim 1, further including:

a wye flow sensor configured to sense flow and pressure of the inspiration and expiration; and a user interface having circuitry and configured and arranged to display a graphical output indicating one or more of the detected inspiration and expiration, the set time between inspirations, the set time between inspirations being exceeded, and characteristics of the delivery of the electrical stimulus.

8. The apparatus of claim 7, wherein the user interface is configured and arranged to generate signals in response to respective user inputs for one or more of setting the time between inspirations, setting characteristics of the electrical stimulus to be delivered, and designating a stimulation breath.

9. The apparatus of claim 7, wherein the controller circuit is configured and arranged with the wye flow sensor to detect inspiration based upon wye flow settings exceeding set trigger flow for inspiration, and to detect expiration based upon a set trigger for expiration.

10. The apparatus of claim 1, wherein the controller circuit is configured and arranged to calculate work of breathing (WOB) indicative of lung compliance and resistance of a patient, and the controller circuit is configured to control the stimulator circuit for delivering the electrical stimulus via the lead system in response to the WOB being less than a predetermined level.

11. The apparatus of claim 1, wherein the controller circuit is configured and arranged to calculate work of breathing (WOB) for assist breaths assisted by a ventilator and spontaneous breaths taken by a patient, as detected by a wye flow sensor, and the controller circuit is configured to control the stimulator circuit to cease the delivery of electrical stimulation if the WOB of one of the assist breaths and the WOB of one of the spontaneous breaths are respectively being-above predetermined levels.

12. The apparatus of claim 1, wherein the controller circuit is configured and arranged to calculate work of breathing (WOB) for breaths, and the controller circuit is configured to control the stimulator circuit to cease the delivery of electrical stimulation if the WOB exceeds a predetermined level.

13. The apparatus of claim 1, wherein the controller circuit is configured and arranged to, in response to detecting a time between inspirations that is shorter than a predetermined time, identify one of the inspirations as a patient-initiated breath and control delivery of the electrical stimulus via the lead system to selectively avoid electrical stimulation when the patient initiates a breath.

14. The apparatus of claim 13, wherein the controller circuit is configured and arranged to, in response to identifying the one of the inspirations as a patient-initiated breath, assess a work of breathing (WOB) corresponding to the patient-initiated breath, and to control the delivery of the electrical stimulus by:

in response to the WOB of the patient-initiated breath being at or exceeding a threshold, prevent delivery of the electrical stimulus, and in response to the WOB of the patient-initiated breath being below the threshold, delivering the electrical stimulus.

15. A method comprising:

detecting inspiration and expiration of a patient exceeding a set trigger flow;

calculating time between the inspirations that exceed the set trigger flow; and delivering electrical stimulus to stimulate the patient's diaphragm via a lead system by, withholding the electrical stimulus in response to the calculated time not exceeding a set time; and applying the electrical stimulus in response to the time that passes after one of the inspirations that exceeds the set trigger flow, and before a subsequent inspiration that exceeds the set trigger flow, exceeding a set time.

16. The method of claim 15, further including calculating work of breathing (WOB) for detected breaths of patient based on lung compliance and resistance of the patient, wherein delivering the electrical stimulus includes delivering the electrical stimulus to a phrenic nerve of the patient based on the calculated WOB.

17. The method of claim 15, further including calculating work of breathing (WOB) for detected breaths of patient based on lung compliance and resistance of the patient; and ceasing delivery of the electrical stimulus in response to the calculated WOB meeting or exceeding a predetermined level.

18. The method of claim 15, further including calculating work of breathing (WOB) for assist breaths taken by the patient and assisted by a ventilator, and for spontaneous breaths taken by the patient; and ceasing the delivery of the electrical stimulus in response to the calculated WOB of one of the assist breaths and the calculated WOB of one of the spontaneous breaths respectively being at or above a predetermined level.

19. The method of claim 15, further including identifying one of the detected inspirations as a patient-initiated breath; and wherein delivering the electrical stimulus includes selectively interrupting delivery of the electrical stimulus in response to detecting the patient-initiated breath.

20. The method of claim 15, further including, in response to identifying one of the inspirations as a patient-initiated breath, assessing a work of breathing (WOB) corresponding to the patient-initiated breath, and controlling the delivering of the electrical stimulus by:

in response to the WOB of the patient-initiated breath being at or exceeding a threshold, interrupt the delivering of the electrical stimulus, and in response to the WOB of the patient-initiated breath being below the threshold, facilitating the delivering of the electrical stimulus.

*21. A percutaneous electrical phrenic nerve stimulation system comprising:*

*a lead system in electrical communication with a stimulator;*

*a controller circuit in operative communication with the lead system and stimulator; and*

*a graphical user interface (GUI) in operative communication with the controller circuit,*

*the controller circuit being configured to calculate work of breathing (WOB) for a patient-initiated breath detected via a flow sensor, the patient-initiated breath including one of an assist breath and a spontaneous breath such that the controller is configured to calculate at least one of an assist breath WOB and a spontaneous breath WOB based on lung compliance and resistance of the patient, and*

*the stimulator configured to deliver electrical stimulation via the lead system, the controller configured to cease the delivery of electrical stimulation from the stimulator if said at least one of the assist breath WOB and spontaneous breath WOB is above a desired level of WOB.*

*22. The system of claim 21, wherein the controller circuit is configured to calculate the work of breathing during a single breath.*

*23. The system of claim 21, wherein the controller circuit is configured to calculate the work of breathing for each patient-initiated breath and each ventilator-initiated breath.*

*24. The system of claim 21, wherein the GUI is configured to output a user alert in response to said at least one of the assist breath WOB and spontaneous breath WOB being below the desired level of WOB.*

*25. The system of claim 24, wherein the patient-initiated breath is the spontaneous breath, and the spontaneous breath is a patient breath during mechanical ventilation that is both initiated and terminated by the patient.*

*26. The system of claim 24, wherein said the patient-initiated breath is the assist breath, and the assist breath is a patient breath during mechanical ventilation that is initiated by the patient and terminated by mechanical ventilation.*

*27. The system of claim 21, wherein the lead system includes first and second leads shaped to reside traverse to first and second phrenic nerves, respectively, each of the first and second leads being connectable to the stimulator via a corresponding lead cable.*

*28. The system of claim 27, wherein each of the first and second leads includes at least four electrodes so that a selected electrode pair of the at least four electrodes are configured to capture a respective one of the first and second phrenic nerves.*

*29. The system of claim 28, wherein the selected electrode pair comprises two electrodes of the at least four electrodes that, when activated, stimulate the respective one of the first and second phrenic nerves to provide a particular WOB level.*

*30. The system of claim 28, wherein each of the first and second leads are percutaneously insertable in a neck of the patient.*

*31. The system of claim 28, wherein the flow sensor comprises a wye sensor in operative communication with the controller circuit and configured to sense flow and pressure of inspiration and expiration during each breath, and wherein the GUI configured and arranged to display a graphical output indicating one or more of the sensed flow and pressure of inspiration and expiration, a time between inspirations, and characteristics of the delivery of the electrical stimulation.*

*32. The system of claim 31, wherein the wye sensor is electrically connectable to the controller circuit via a cable.*

*33. The system of claim 28, wherein the GUI includes a touch screen display device that displays user input fields to receive stimulation settings for the selected electrode pair of each of the first and second leads.*

*34. The system of claim 21, wherein the GUI includes a touch screen display device that displays user input fields to receive mechanical ventilator settings and input values for the lung compliance and resistance for the patient.*

*35. The system of claim 21, wherein the GUI includes a touch screen display device includes a stimulation indicator that activates during application of the electrical stimulation via the lead system.*

*36. The system of claim 21, wherein the GUI is configured to output a user alert in response to the unstimulated work of breathing being greater than the unstimulated WOB stop limit.*

*37. The system of claim 21, wherein the GUI includes a user-selectable setting that causes the stimulator to deliver electrical stimulation via the lead system during mandatory breaths only.*

*38. A percutaneous electrical phrenic nerve stimulation system comprising:*

*a lead system in electrical communication with a stimulator and configured to stimulate at least one of first and second phrenic nerves during selected breaths of a patient;*

*a controller circuit in operative communication with the lead system and stimulator, the controller circuit being configured to calculate an unstimulated work of breathing detected via a flow sensor during an unstimulated breath of a patient; and*

*a graphical user interface (GUI) in operative communication with the controller circuit, the GUI including a user setting indicative of an unstimulated WOB stop limit,*

*wherein the stimulator is configured to deliver electrical stimulation via the lead system, and the controller configured to cease the delivery of the electrical stimu-*

*lation during unstimulated breaths after identifying that the unstimulated work of breathing is greater than the unstimulated WOB stop limit.*

* * * * *